(12) United States Patent
Hamrick

(10) Patent No.: US 9,631,209 B1
(45) Date of Patent: Apr. 25, 2017

(54) METHOD FOR FERMENTING STALKS OF THE POACEAE FAMILY

(71) Applicant: Edward Brian Hamrick, Sunny Isles Beach, FL (US)

(72) Inventor: Edward Brian Hamrick, Sunny Isles Beach, FL (US)

( * ) Notice: Subject to any disclaimer, the term of this patent is extended or adjusted under 35 U.S.C. 154(b) by 0 days.

(21) Appl. No.: 15/424,843

(22) Filed: Feb. 4, 2017

Related U.S. Application Data

(60) Provisional application No. 62/349,674, filed on Jun. 14, 2016.

(51) Int. Cl.
| | | |
|---|---|---|
| C12P 7/06 | (2006.01) | |
| C12P 7/14 | (2006.01) | |
| C12P 5/02 | (2006.01) | |

(52) U.S. Cl.
CPC ............... *C12P 7/14* (2013.01); *C12P 5/023* (2013.01)

(58) Field of Classification Search
None
See application file for complete search history.

(56) References Cited

U.S. PATENT DOCUMENTS

| | | | | |
|---|---|---|---|---|
| 9,194,012 | B2 * | 11/2015 | Hamrick | C12P 19/02 |
| 9,428,772 | B2 * | 8/2016 | Hamrick | C12P 19/02 |
| 9,499,839 | B2 * | 11/2016 | Malshe | C12P 7/14 |
| 2014/0053827 | A1 * | 2/2014 | Macedo Baudel | C12P 7/10 127/30 |

FOREIGN PATENT DOCUMENTS

CN 103571879 * 2/2012

OTHER PUBLICATIONS

Ohgren, K. et al. Fuel Ethanol Production from Steam Pretreated Corn Stover Using SSF at Higher Dry Matter Content. Biomass & Bioenergy 30(10)863-869, 2006.*
Nasidi M. et al. Improved Production of Ethanol Using Bagasse from Different Sorghum Cultivars. Biomass & Bioenergy 72:288-299 2015.*

* cited by examiner

*Primary Examiner* — Ralph Gitomer
(74) *Attorney, Agent, or Firm* — O'Connor & Company; Ryan P. O'Connor

(57) ABSTRACT

A method for fermenting stalks of the Poaceae family is provided. This includes sugarcane, sorghum and maize stalks. This method compresses stalks between rollers to between 20% and 90% of their diameter while the stalks are submerged in an aqueous reagent solution. This fractures the stalks in the axial direction without significant loss of juice while simultaneously pulling the reagent solution into the resulting network of cracks in the parenchyma tissue. In some variants, the aqueous reagent solution contains fermentation organisms, the sugars diffuse from the parenchyma cells, come into contact with the fermentation organisms located in the cracks in the stalks and produce ethanol and lactic acid within the stalks. In some variants, combinations of enzymes, acids and Fenton reagent in the aqueous reagent solution diffuse into and degrade the lignocellulosic matrix in the stalks.

20 Claims, 1 Drawing Sheet

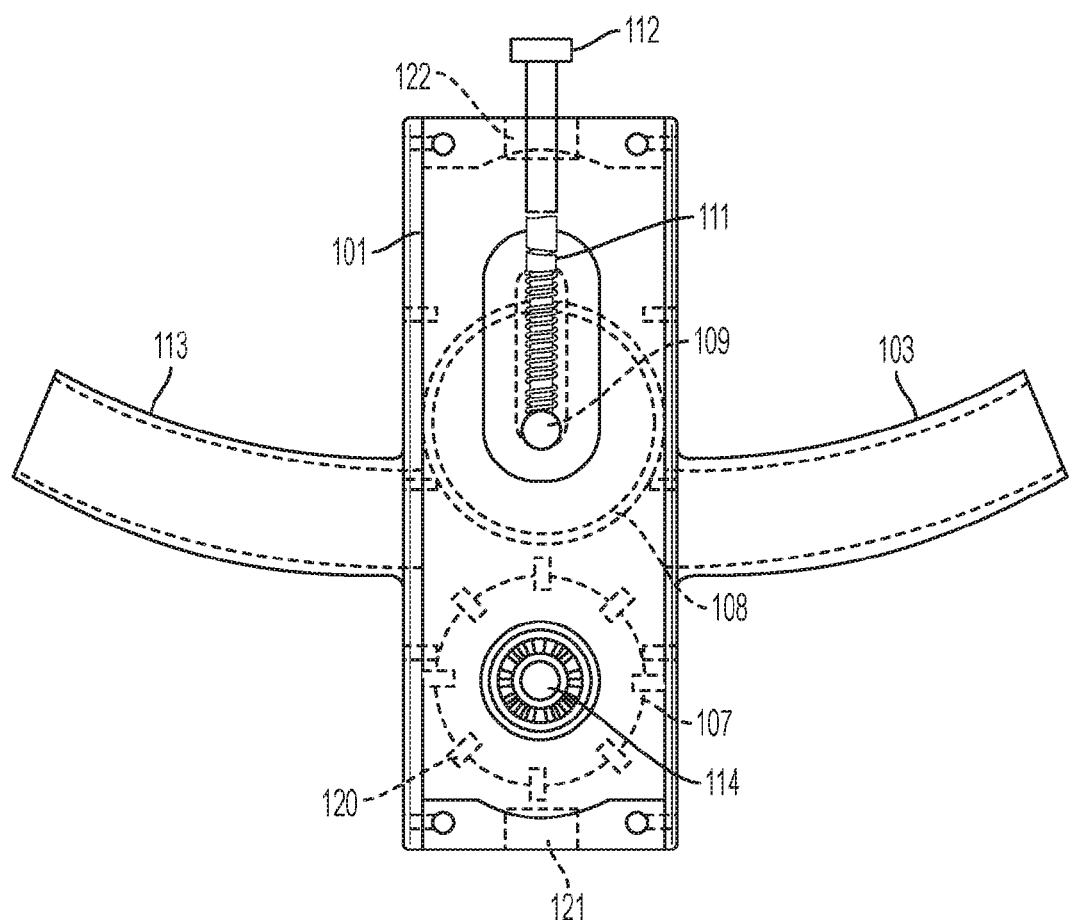

METHOD FOR FERMENTING STALKS OF THE POACEAE FAMILY

PRIORITY DATA

This patent application is a non-provisional application with priority to U.S. Provisional Patent App. No. 62/349,674, filed Jun. 14, 2016, which is hereby incorporated by reference herein.

FIELD OF THE INVENTION

The present invention pertains to fermentation processes to synthesize a desired chemical compound. More specifically, the invention pertains to preparation of oxygen-containing organic compounds with multiple types of microorganisms.

BACKGROUND OF THE INVENTION

The most widely cultivated crops of the Poaceae family are sugarcane (*Saccharum officinarum*), sorghum (*Sorghum bicolor*) and maize (*Zea mays*). The word Poaceae is derived from the Ancient Greek πόα (póa), meaning "fodder". The stalks of crops in the Poaceae family have been used as animal fodder for millennia. These stalks are eaten by ruminants, including cattle, sheep and goats, because ruminants can digest cellulose and hemicellulose. These stalks also contain sugars in the storage parenchyma cells and sometimes contain lesser amounts of starch granules in the storage parenchyma cells.

The sugars in these stalks have long been used to produce table sugar and molasses, and have long been fermented to ethanol to make drinking ethanol (e.g. rum) and fuel ethanol. These stalks are also often ensiled by sprinkling them with lactic acid bacteria, a process that preserves the stalks for up to a year as animal feed and that makes the stalks more digestible by ruminants.

Ensiling has been practiced for about 200 years since it was discovered (in Germany) that when one chops grasses and compresses the chopped grasses so air is kept out, that the chopped (ensiled) grasses don't "spoil" (i.e. smell like vinegar). Even today, ensiling grasses and other crops of the Poaceae family involves first chopping the stalks into small pieces about 12 to 25 mm long, then sprinkling with microorganisms (mostly lactic acid bacteria), then compressing the chopped stalks to keep air out.

This only works because the sugars can diffuse to the cut surfaces of the chopped stalks so that the lactic acid bacteria can consume the sugars. Most yeast and most lactic acid bacteria aren't motile (can't move on their own), so sugar must diffuse to them (these microorganisms can't swim to where the sugars are). Because they aren't motile, and because the stalks of the Poaceae family aren't easily penetrated by microorganisms, stalks must be either chopped or crushed to let the sugars diffuse to the microorganisms.

Sprinkling microorganisms and enzymes onto chopped or crushed stalks only deposits microorganisms and enzymes on the outer surfaces of the stalks. The cracks that are formed when stalks are chopped or crushed contain air bubbles that remain fixed in the cracks, preventing microorganisms and enzymes from being deposited within the cracks when sprinkled on the stalks. Since yeast and lactic acid bacteria aren't motile, and since the diffusion of enzymes and microorganisms is extremely slow, the penetration of the stalks by yeast, lactic acid bacteria and enzymes is poor.

There's a need in the art for a solution to this problem of incomplete penetration of the stalks by yeast, lactic acid bacteria and especially enzymes.

SUMMARY OF THE INVENTION

The invention in some variations provides a method for fermenting stalks of the Poaceae family, the method comprising the steps of:

(a) providing stalks of the Poaceae family, wherein the stalks have an average length greater than 100 mm, and wherein the stalks have an average initial moisture content between 25% and 80%;

(b) compressing the stalks between rollers while the stalks are submerged in an aqueous reagent solution, wherein the rollers compress the average diameter of the stalks by between 20% and 90%, and wherein the aqueous reagent solution contains one or more fermentation organisms selected from the group consisting of yeasts, lactic acid bacteria, acetic acid bacteria, and combinations thereof;

(c) removing the stalks from the aqueous reagent solution, wherein the stalks retain at least a portion of the one or more fermentation organisms; and (d) fermenting the stalks for a fermentation time to produce fermentation products within the stalks.

In preferred embodiments, the stalks are selected from the group consisting of sugarcane stalks, sorghum stalks and maize stalks.

In some embodiments, the stalks have leaves attached to the stalks.

In some embodiments, the stalks are present as a whole plant.

In preferred embodiments, the rollers have a tangential velocity between 0.1 m/s and 10 m/s.

In preferred embodiments, the aqueous reagent solution contains enzymes selected from the group consisting of pectin lyase, amylase, cellulase, glucose oxidase, hexose oxidase, xylanase and combinations thereof.

In some embodiments, the aqueous reagent solution contains acids selected from the group consisting of formic acid, acetic acid, lactic acid and combinations thereof.

In some embodiments, the aqueous reagent solution contains ferrous ions, hydrogen peroxide, or a combination thereof.

In preferred embodiments, the fermentation time is between 1 day and 7 days.

In preferred embodiments, the yeast is a strain of *Saccharomyces cerevisiae*.

In some embodiments, the stalks are dehydrated during the fermentation lag time of step (d).

In some embodiments, the lactic acid bacteria are selected from the group consisting of *Lactobacillus plantarum, Lactobacillus buchneri, Pediococcus pentosaceus, Pediococcus acidilactici, Propionibacterium freudenreichii* and combinations thereof.

In preferred embodiments, the method further comprises mixing the aqueous reagent solution using turbulent energy from 0.15 W/kg to 5 W/kg.

In some embodiments, the method further comprises maintaining the stalks in an anaerobic environment for an ensiling time subsequent to the completion of the fermentation time.

In some embodiments, the ensiling time is between one day and one year.

In preferred embodiments, the method further comprises recovering the fermentation products by crushing the stalks.

In some embodiments, the method further comprises recovering the fermentation products by evaporation of the fermentation products from the stalks.

In some embodiments, the method further comprises feeding the stalks to ruminants subsequent to step (d).

In some embodiments, the method further comprises using the stalks with anaerobic digestion to produce methane subsequent to step (d).

In some embodiments, the method further comprises using the stalks with enzymatic hydrolysis to produce ethanol from cellulose subsequent to step (d).

BRIEF DESCRIPTION OF THE DRAWING

FIG. 1 is a schematic drawing of an experimental apparatus used in embodiments and examples of the present invention.

DETAILED DESCRIPTION OF EMBODIMENTS OF THE INVENTION

The methods, processes, and systems of the present invention will be described in detail by reference to various non-limiting embodiments and FIGURE(s).

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing parameters, conditions, results, and so forth used in the specification and claims are to be understood as being modified in all instances by the term "about." Accordingly, unless indicated to the contrary, the numbers set forth in the following specification and attached claims are approximations that may vary depending upon specific algorithms and calculations.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

No embodiments described herein shall be limited by any theory or speculation regarding reaction mechanisms, mass-transfer mechanisms, or descriptions of feedstocks or products.

The present invention is premised on a technical solution to the problem that producing fermentation products from sugar-rich plant parenchyma tissue is expensive because of the large amount of energy and capital required for efficiently crushing stalks of the Poaceae family to extract sugars. The present invention is also premised on a technical solution to the problem of degradation of stalks of the Poaceae family after harvesting and before processing or consumption.

The terms "compress", "compressed", "compressing", and "compression" are used herein to indicate that the average diameter of stalks is reduced by 20% to 90%. The terms "crush", "crushed" and "crushing" are used herein to indicate that the average diameter of stalks is reduced by more than 90%.

This invention uses the technical approach of compressing the average diameter of stalks by between 20% and 90% while the stalks are submerged in a reagent solution containing one or more fermentation organisms. This compression fractures the stalks without significant loss of sugars and the reagent solution is pulled into the resulting cracks in the parenchyma tissue. The sugars diffuse from the parenchyma cells, come into contact with the fermentation organisms located in the cracks and produce ethanol and/or lactic acid within the stalks. The ethanol and/or lactic acid preserve the stalks for subsequent extraction of ethanol and/or consumption as fodder for ruminants. In some variants, enzymes in the reagent solution degrade and separate the parenchyma cell walls for lower-energy crushing to extract ethanol or sugars.

Principles of the invention are demonstrated in the Examples herein.

The low pH that results from lactic acid bacteria fermenting sugars in the crops prevents other spoilage organisms from growing. Keeping the crop anaerobic prevents acetic acid bacteria from consuming ethanol and producing acetic acid (vinegar). Since acetic acid bacteria are highly motile, they can consume all the ethanol in ensiled stalks unless the environment is kept anaerobic (oxygen free).

It is now thought that the low pH caused by lactic acid bacteria also results in a type of dilute acid hydrolysis of the hemicellulose in the stalks, which improves the digestibility of the stalks. Normally dilute acid hydrolysis is performed in a few hours at pH 2.0 or less, but at pH 4.0 in silage, this dilute acid hydrolysis is performed in weeks or months. The data supporting dilute acid hydrolysis in silage is described in Henk, Linda L., and James C. Linden, "Solid-state production of ethanol from sorghum." *Applied biochemistry and biotechnology* 57.1 (1996): 489-501, which is hereby incorporated by reference herein. Henk notes (on page 491; internal citations omitted) that "Our data show that ensiling is a form of dilute-acid hydrolysis. Ensiling improved the reactivity of the lignocellulosic fibers to enzymatic hydrolysis."

Those skilled in the art will recognize that many microorganisms and enzymes are commonly used to ensile crops, including yeast, lactic acid bacteria, hemicellulase, cellulase and glucose oxidase. This is described in Kung, L, "Silage fermentation and additives," *Proceedings of Alltech's Seventeenth Annual Symposium.* 2001, which is hereby incorporated by reference herein. This is also described in Charley, Robert C., PCT Patent Application PCT/CA2010/001729, which is hereby incorporated by reference herein.

Those skilled in the art, and those who are familiar with freshly harvested sugarcane, sorghum and maize, will recognize that the freshly harvested stalks of these crops are quite brittle. If an average person steps with his heel on a stalk laid on the ground, he will feel it crack, and looking at the compressed stalk he will see a large crack, a few smaller cracks, and a large number of even smaller cracks, all of these cracks in the axial direction. He will also see that little juice is squeezed out of the stalk by simply stepping on a stalk with his heel. He will also recognize that a bent stalk will suddenly break with a snap (brittle failure)—as in the well-known "green snap" failure in corn crops. This invention takes advantage of the brittle nature of freshly harvested stalks to propagate cracks in the stalks with very little energy.

The storage parenchyma cells in stalks of the Poaceae family are thin-walled polyhedral cells approximately 360 microns long and 60 microns in diameter with a wall thickness of about 2 microns. This is described in more detail in Dong, "A nitrogen-fixing endophyte of sugarcane stems (a new role for the apoplast)," *Plant Physiology* 105.4 (1994): 1139-1147, which is hereby incorporated by reference herein.

In particular, Dong shows in FIG. 2, pictures C and G, that the sugarcane parenchyma cells are aligned in the axial direction, but aren't aligned in the radial direction. This is why water flows through the apoplast in the axial direction (limited by the internode length) but doesn't flow through the apoplast in the radial or lateral directions. The parenchyma cells of other stalks in the Poaceae family are similarly aligned. Sugarcane and other stalks in the Poaceae family fracture easily in the axial direction because the parenchyma cell walls form fracture planes in the axial direction. Stalks in the Poaceae family are difficult to cut in the radial direction because the cell walls aren't aligned in the radial direction, forcing cutting through the cell walls. By contrast, stalks in the Poaceae family don't require much energy to split or crack in the axial direction.

Stalks in the Poaceae family are easily cracked open when compressed radially. The results of cracking of sugarcane stalks, along with a finite element model of cracking, are contained in Skantz, J., and S. A. Domanti, "Experiments into the constitutive behaviour of sugarcane billets." *PROCEEDINGS-AUSTRALIAN SOCIETY OF SUGAR CANE TECHNOLOGISTS. WATSON FERGUSON AND COMPANY,* 1998, which is hereby incorporated by reference herein. Without wishing to be bound by any particular theory, it is believed that initial radial compression produces one large crack, subsequent compression produces two smaller cracks, subsequent compression produces four even smaller cracks, etc.

Stalks in the Poaceae family that are cracked open when compressed quickly return to a round shape when the force on the stalk is removed. The fibers in the stalks have a high tensile strength and serve to pull the stalk back to a round shape when the force on the stalks is removed, albeit with cracks in the parenchyma tissue of the stalk.

Juice in the parenchyma cells of stalks of the Poaceae family generally contain between 2% and 20% hexose sugars, primarily consisting of sucrose, glucose and fructose. The parenchyma tissue also often contains starch granules. The dry matter of these stalks, after squeezing out the juice, is often referred to as bagasse. Bagasse generally comprises approximately 35% cellulose, 25% hemicellulose and 22% lignin. The hemicellulose typically consists of about 85% xylose, 13% glucose and 2% arabinose. The cellulose, hemicellulose and lignin are often tightly bound together, preventing access of enzymes to hydrolyze the cellulose and hemicellulose. Ensiling (converting free sugars to lactic acid) is a form of dilute acid hydrolysis that hydrolyzes hemicellulose, making the cellulose more accessible to enzymes in ruminant digestion, anaerobic digestion or enzymatic hydrolysis.

The starch content of sweet sorghum stems is described in Zhao, Ya Li, et al., "Changes in stem composition and harvested produce of sweet sorghum during the period from maturity to a sequence of delayed harvest dates," *Biomass and Bioenergy* 39 (2012): 261-273, which is hereby incorporated by reference herein. Zhao shows, in Table 2, that stalks have about 10.1% of their weight in sugars and 3.6% of their weight in starch. If the starch were expressed in the juice, the juice would have about 4.3% of its weight in starch, but studies show that the juice only has about 0.1% of its weight in starch (1000 mg/L). Without wishing to be bound by any particular theory, it is believed that most of the starch is left behind in the stalks when the juice is squeezed out, because of the filtering of the starch granules when the stalks are under extreme pressure.

The starch content of sugarcane and sweet sorghum juice is described in Alves, Fernanda Viginotti, et al., "Structural and physicochemical characteristics of starch from sugar cane and sweet sorghum stalks," *Carbohydrate polymers* 111 (2014): 592-597, which is hereby incorporated by reference herein. Alves shows that sugarcane juice has about 356 mg/L of starch and sweet sorghum juice has about 1147 mg/L of starch. This implies that sugarcane stalks have about one third as much starch as sweet sorghum stalks, and therefore about 1% of the weight of a sugarcane stalk is starch.

The sugar content of tropical maize hybrids is described in White, Wendy G., et al., "The sugar, biomass and biofuel potential of temperate by tropical maize hybrids," *GCB Bioenergy* 4.5 (2012): 496-508, which is hereby incorporated by reference herein. White shows that hybrids of temperate and tropical maize (*Zea mays*) produce both grain and fermentable stalk sugars.

Many fermentation organisms can directly convert glucose, fructose, maltose (glucose dimer) and sucrose (glucose-fructose dimer) to ethanol and lactic acid. Herein, monomers and dimers of glucose and fructose will be referred to as sugars, fermentation organisms that convert sugars to ethanol will be referred to as yeasts and fermentation organisms that convert sugars to lactic acid will be referred to as lactic acid bacteria. Fermentation organisms that convert sugars to ethanol can be either eukaryotic, single-celled organisms or can be bacteria. Fermentation organisms that convert sugars to lactic acid can be either eukaryotic, single-celled organisms or can be bacteria.

Many fermentation organisms convert sugars to ethanol. The most widely used fermentation organisms that produce ethanol, brewer's yeasts, are strains of *Saccharomyces cer-*

*evisiae*. Ethanol has significant economic value in beverages, transportation fuels and precursors for other organic compounds.

Other fermentation organisms convert sugars to lactic acid. These are known as lactic acid bacteria and the most common strain is *Lactobacillus plantarum*. Lactic acid reduces the pH of what is being fermented to about 4.2 which inhibits the growth of most other bacteria and fungi. This is commonly used to preserve foods such as yogurt and sauerkraut. This is also commonly used to preserve crops for later use as animal feed (fodder), known as "ensiling".

Some organisms convert ethanol to acetic acid (vinegar) in the presence of oxygen (aerobic environments). The most common strain is *Acetobacter aceti*.

A 0.5% solution of formic acid is a selective inhibitor of lactic acid bacteria as well as other contaminating bacteria, but doesn't inhibit yeast. This is described in Schmidt, J., et al., "Preservation of sugar content in ensiled sweet sorghum," *Bioresource Technology* 60.1 (1997): 9-13, which is hereby incorporated by reference herein. A large percentage of the formic acid produced worldwide is used for ensiling animal feed.

The inhibition of *Saccharomyces cerevisiae* by lactic acid and acetic acid is described in Narendranath, N. V., K. C. Thomas, and W. M. Ingledew, "Effects of acetic acid and lactic acid on the growth of *Saccharomyces cerevisiae* in a minimal medium." *Journal of Industrial Microbiology and Biotechnology* 26.3 (2001): 171-177, which is hereby incorporated by reference herein. Narendranath notes that "When 0.5% w/v lactic acid was present in the media, the presence of even 0.04% w/v acetic acid (which did not cause a significant change in yeast growth rate when present by itself) caused a significant reduction in the growth rate of *S. cerevisiae*".

The boiling point of ethanol is 78° C., the boiling point of lactic acid is 122° C. and the boiling point of acetic acid is 118° C. This makes it possible for low-cost separation of ethanol from solutions containing lactic acid and acetic acid by using a pot still (sometimes called an alembic). However, the boiling point of formic acid is 100.8° C., which makes it more difficult to separate a mixture of ethanol and formic acid using a pot still. Methanol is also produced in limited amounts by fermentation organisms and some enzymes, and has a boiling point of 65° C. Since it boils at a lower temperature than ethanol, it can be removed using a pot still by discarding the initial few percent of the distillate (called the heads). Both formic acid and methanol are toxic to humans, so if beverage alcohol is produced from fermented stalks, formic acid shouldn't be used to ensile the stalks.

There are well-known techniques for fermenting the sugars in stalks of the Poaceae family to ethanol. Stalks are generally crushed between a series of rollers to extract the juice by bursting the parenchyma cells, and then the juice is separated from residual solids and fermented. Because the parenchyma cells are so small, it takes a lot of energy to crush them. Almost 35% of the capital and operating costs of producing sugar from stalks is due to the cost of crushing. The economics of crushing sugarcane is described in more detail in Gbaboa, "Comparative study on cane cutter/juice expeller and roller model Sugarcane juice extraction systems," *INT J CURR SCI* 2013, 7: E 55-60, which is hereby incorporated by reference herein.

Solid-state fermentation is sometimes used to ferment stalks of the Poaceae family, cutting the stalks into small pieces (or shredding the stalks), sprinkling them with yeast and letting them ferment. The yeast adheres to the newly exposed parenchyma tissue and the sugars from within the chopped pieces (or shredded stalks) diffuse to the yeast, which ferments the sugars to ethanol. This is the same mechanism as ensiling, but where lactic acid bacteria is used instead of yeast. The disadvantage of this type of solid-state fermentation is that it requires a lot of energy to pasteurize the stalks before fermenting. Another disadvantage of this technique is the large amount of energy needed to cut or shred the stalks. Another disadvantage of this technique is that it doesn't allow reacting the interior of the stalks with enzymes, because of the very slow diffusion of enzymes. Another disadvantage is that chopped or shredded stalks have a much lower bulk density than whole stalks or billets.

One example of this is the EX-FERM process, described in U.S. Pat. No. 4,560,659, issued Dec. 24, 1985 to Asturias, which is hereby incorporated by reference herein. The EX-FERM process involves chopping the sugarcane to pieces with an average particle size diameter between 0.25 cm to 4.0 cm, mixing with yeast and water and fermenting. The fermented solution is then reused in subsequent fermentations to increase the concentration of ethanol before distillation.

Another type of solid-state fermentation is described in Bryan, William L., "Solid-state fermentation of sugars in sweet sorghum," *Enzyme and Microbial Technology* 12.6 (1990): 437-442, which is hereby incorporated by reference herein. This technique cuts the stalks to 0.6 cm lengths or shreds the stalks. Almost 80% of the sugar in the stalks is fermented to ethanol. However, large amounts of lactic acid and acetic acid are produced because the stalks weren't pasteurized before fermentation.

A similar type of solid-state fermentation is described in Henk, Linda L., and James C. Linden, "Solid-state production of ethanol from sorghum," *Applied biochemistry and biotechnology* 57.1 (1996): 489-501, which is hereby incorporated by reference herein. This technique uses a forage chopper to chop both the stalks and leaves in the field, sprinkle the chopped forage with yeast and enzymes, and then allow to ferment. A disadvantage is that countercurrent extraction is needed to extract ethanol, which is a more capital-intensive method than crushing stalks. Henk notes (on page 500) that "Ethanolic sorghum silage is stable over a period of at least 230 d, thus potentially producing a low-cost feedstock for continuous ethanol production on a yearly basis."

Another technique for fermenting the sugars in stalks of the Poaceae family to ethanol is described in U.S. Pat. No. 9,499,839, issued Nov. 22, 2016 to Hamrick, which is hereby incorporated by reference herein and which is commonly owned with the present application. This technique uses vacuum to infuse yeast and enzymes into the apoplast of carbohydrate-rich crops, including sugarcane and sweet sorghum, draining the liquid from around the crops, and then fermenting within the apoplast.

Stalks in the Poaceae family can be digested by ruminants after ensiling. Henk asserts that this improved digestibility is caused by dilute acid hydrolysis of hemicellulose. Digestibility of sweet sorghum is described in Di Marco, O. N., et al., "Digestibility of forage silages from grain, sweet and bmr sorghum types: Comparison of in vivo, in situ and in vitro data," *Animal Feed Science and Technology* 153.3 (2009): 161-168, which is hereby incorporated by reference herein. Digestibility of sugarcane is described in Kawashima, T., et al., "Feeding value of sugarcane stalk for cattle," *ASIAN AUSTRALASIAN JOURNAL OF ANIMAL SCIENCES* 15.1 (2002): 55-60, which is hereby incorporated by reference herein. Digestibility of corn stover stalks is described in Tolera, Adugna, and Frik Sundstøl, "Morphological fractions of maize stover harvested at different stages of grain maturity and nutritive value of different fractions of the stover," *Animal Feed Science and Technology* 81.1 (1999): 1-16, which is hereby incorporated by reference herein.

Digestibility and nutrient value of ensiled grasses is described in Jaakkola, Seija, Pekka Huhtanen, and K. Hissa, "The effect of cell wall degrading enzymes or formic acid on fermentation quality and on digestion of grass silage by cattle," *Grass and Forage Science* 46.1 (1991): 75-87, which is hereby incorporated by reference herein. Jaakkola concludes that when timothy grass (*Phleum pretense*, in the Poaceae family) contains insufficient sugars for ensiling with lactic acid bacteria, that ensiling with formic acid works better than ensiling with cellulase and hemicellulase enzymes.

Most fermentation organisms oxidize sugars to carbon dioxide and water in an aerobic (with oxygen) environment. One mole of glucose or fructose ($C_6H_{12}O_6$) (or 0.5 mole of sucrose or maltose) and six moles of oxygen ($O_2$) are oxidized to six moles of carbon dioxide ($CO_2$) and six moles of water ($H_2O$). This mechanism rapidly removes oxygen from the environment when fermenting.

Yeasts ferment sugars to ethanol in an anaerobic (without oxygen) environment. One mole of glucose or fructose (or 0.5 mole of sucrose or maltose) is fermented to 2 moles of ethanol and 2 moles of carbon dioxide and gives off 118 kJ of heat. This means that fermenting an 18% sugar solution will result in a temperature rise of 34° C., which means that cooling of the fermentation medium is required. Fermenting 1 liter of an 18% sugar solution (1 mole of glucose) will also produce 2 moles of carbon dioxide, which has a volume of about 48 liters at 20° C. and atmospheric pressure. A typical yeast ferments most efficiently between 20° C. and 40° C. but has significant fermentation activity down to 5° C. (white wine is fermented between 7° C. and 15° C.). Yeast cells die gradually at temperatures above 42° C. *Saccharomyces cerevisiae* is relatively insensitive to pH and will ferment in a pH range from 2.9 to 7.2. This is described in more detail in Arroyo-López, "Effects of temperature, pH and sugar concentration on the growth parameters of *Saccharomyces cerevisiae*, *S. kudriavzevii* and their interspecific hybrid," *International journal of food microbiology* 131.2 (2009): 120-127, which is hereby incorporated by reference herein.

Lactic acid bacteria ferment sugars to lactic acid in both aerobic and anaerobic environments, depending on the type of lactic acid bacteria. In a homo-lactic fermentation, one mole of glucose or fructose ($C_6H_{12}O_6$) (or 0.5 mole of sucrose or maltose) is fermented to two moles of lactic acid ($C_3H_6O_3$). In a hetero-lactic fermentation, one mole of glucose or fructose ($C_6H_{12}O_6$) (or 0.5 mole of sucrose or maltose) is fermented to one mole of lactic acid ($C_3H_6O_3$), one mole of ethanol ($C_2H_6O$) and one mole of carbon dioxide ($CO_2$). *Lactobacillus plantarum* grows at between 15° C. to 40° C. in both aerobic and anaerobic environments. In aerobic environments, *Lactobacillus plantarum* respires oxygen and this consumed oxygen produces hydrogen peroxide ($H_2O_2$), which inhibits the growth of other organisms.

Most *Saccharomyces cerevisiae* strains have a diameter of approximately 10 microns. A *Saccharomyces cerevisiae* strain with a cell size of approximately 5 microns is Thermosacc® Dry, available from Lallemand Biofuels & Distilled Spirits, Duluth, Ga., USA. It produces ethanol concentrations up to 20% by volume (16% by weight), so sugar-rich crops with up to 32% sugar by weight can be fermented by this yeast. This means that a crop or extracted juice can be dehydrated before fermenting so that the resulting ethanol concentration is higher. Yeast fermentation can take from 1 hour to 8 hours before significant production of ethanol and carbon dioxide. This is commonly called the fermentation lag time. Dehydration during the fermentation lag time can increase the final ethanol concentration.

Most *Lactobacillus plantarum* strains are rod-shaped with a diameter of about 0.5-1.2 micron and a length of 1-10 microns. One source of *Lactobacillus plantarum* is BIO-TAL® Silage Inoculant II, available from Lallemand Animal Nutrition, Milwaukee, Wis., USA. Often *Lactobacillus plantarum* is used with other bacteria and enzymes for treating silage. This is described in U.S. Pat. No. 5,432,074, issued Jul. 11, 1995 to Evans et al., which is hereby incorporated by reference herein. Currently available ensiling formulations from Lallemand Animal Nutrition contain mixtures of *Lactobacillus plantarum* with *Lactobacillus buchneri*, *Pediococcus pentosaceus*, *Pediococcus acidilactici* and *Propionibacterium freudenreichii*.

Fermentation organisms are so large that they don't move by diffusion in their lifetime. However, gasses and sugars diffuse easily, and easily diffuse through the parenchyma cell walls, and enzymes diffuse through liquids external to the parenchyma cells. The diffusion coefficient of carbon dioxide is $2.5 \times 10^{-9}$ $m^2/s$, which means it diffuses 1 mm in about 7 minutes and 10 mm in about 11 hours. The diffusion coefficient of sucrose is $7.1 \times 10^{-10}$ $m^2/s$, which means it diffuses 1 mm in about 17 minutes and 10 mm in about 39 hours. The diffusion coefficient of pectin lyase is $8.0 \times 10^{-11}$ $m^2/s$, which means it diffuses 1 mm in about 3.5 hours and 10 mm in about 14 days.

Yeast cells adhere to surfaces (such as parenchyma cells) in the presence of sugars. This is described Verstrepen and Klis, "Flocculation, adhesion and biofilm formation in yeasts," *Molecular microbiology* 60.1 (2006): 5-15, which is hereby incorporated by reference herein. Similarly, lactic acid bacteria also adhere to surfaces such as parenchyma cells.

Yeast and lactic acid bacteria are both sold in freeze-dried form and are easy to handle. Both are classified as GRAS (Generally Recognized as Safe) and are commonly consumed in the average diet—for example, bread is made with *Saccharomyces cerevisiae* yeast and yogurt is made with *Lactobacillus plantarum* (which is also present in saliva) and *Lactobacillus acidophilus*. Similarly, pectin lyase, amylase, cellulase, glucose oxidase, hexose oxidase and xylanase enzymes are available in food-grade form.

Starch is a polymer of glucose. Before starch can be converted by yeast to ethanol or by lactic acid bacteria to lactic acid, it must first be converted to glucose by amylase enzymes. Starch is insoluble in water in the temperature range for which yeast or lactic acid bacteria is active.

There are amylases available that convert starch to glucose efficiently in the temperature range that yeast operates efficiently. One example is the STARGEN® 002 enzyme formulation from DuPont Industrial Biosciences, USA. This contains an *Aspergillus kawachi* alpha-amylase expressed in *Trichoderma reesei* and a gluco-amylase from *Trichoderma reesei* that work synergistically to hydrolyze granular starch substrate to glucose. The endo-activity, alpha-amylase and exo-activity, gluco-amylase catalyze the complete hydrolysis of granular starch under a variety of ethanol fermentation conditions. STARGEN® 002 has significant activity between 20° C. and 40° C., and between pH 3.5 and 4.5, so it's suitable for the pH and temperature of yeast Parenchyma tissue can be macerated (cells separated from each other) by enzymes. When the parenchyma tissue is macerated, the cell membrane is also breached, both from mechanical action and from enzymes that are released from the cell wall. This causes the contents of the vacuoles to leak out of the parenchyma cells and causes enzymes to more easily diffuse into the vacuoles. This also provides a retting action, where the liquid in the parenchyma cells can be more easily removed by squeezing or evaporation. Pectin lyase and xylanase macerate parenchyma cells in Poaceae stalks. This is described in Ishii, "Enzymes for the isolation of protoplasts," *Plant Protoplasts and Genetic Engineering* I. Springer Berlin Heidelberg, 1989, 23-33, which is hereby incorporated by reference herein. Ishii also shows that cellulose also results in cell wall degradation.

Pectin lyase degrades pectin without producing methanol as a byproduct. This makes the fermented juice more useful as a higher-value ethanol product of this invention. There are pectin lyases available that operate in the same pH and temperature range as yeast, in particular pectin lyase from *Aspergillus niger*, with an optimum pH of 5.5 and an optimum temperature of 35° C. However, pectin lyase is unusual in that it has significant activity at temperatures as low as 5° C. Pectin lyase is described in Yadav et al., "Pectin lyase: a review," *Process Biochemistry* 44.1 (2009): 1-10, which is hereby incorporated by reference herein. Two examples of pectin lyase that operate in the same pH and temperature range of yeast are "Pectinex® XXL" (Novozymes A/S, Denmark) and "Rohapect 10L" (AB Enzymes GmbH, Germany).

Ishii also shows that xylanase macerates parenchyma cells of stalks from Poaceae stalks and cellulase bursts open the cell walls of parenchyma cells of these stalks. An example of a commercially available xylanase is HTec3 (Novozymes A/S, Denmark), which is a mixture of endoxylanase and cellulase. HTec3 has about 90% activity at temperatures below 30° C. and about 70% activity at a pH of 4.0, so it's suitable for the pH and temperature of yeast.

Glucose oxidase converts glucose and $O_2$ to gluconic acid and hydrogen peroxide. A combination of glucose oxidase and cellulase has been shown to prevent the degradation of grass silage in aerobic conditions. This is described in Rauramaa, A. L., J. J. Setala, and A. E. A. Tommila, "The effect of glucose oxidase on the preservation of grass silage," *Grass and Forage Science* 46.4 (1991): 359-364, which is hereby incorporated by reference herein. Glucose oxidase is active in a broad range of pH and temperatures, which is described in Biyela, B. N. E., et al, "The production of reduced-alcohol wines using Gluzyme Mono® 10.000 BG-treated grape juice," *S. Afr. J. Enol. Vitic.*, Vol. 30, No. 2, (2009): 124-132, which is hereby incorporated by reference herein. Without wishing to be bound by any particular theory, it is believed that cellulase releases glucose from hard to hydrolyze cellulose, and this slow release of glucose results in slow production of gluconic acid and hydrogen peroxide, where the combined effect of lower pH due to gluconic acid and the toxicity of hydrogen peroxide prevents most contaminating organisms from producing lactic acid and acetic acid.

When fermenting, yeast produces large amounts of carbon dioxide ($CO_2$). Carbonic acid is formed by the dissolution of $CO_2$ in water. When fermenting, the partial pressure of $CO_2$ is 100 kPa (1 atm) and the pH of this solution is about 3.92. Yeast ferments well at this pH, pectin lyase enzymes from *Aspergillus niger* (such as Pectinex® XXL and Rohapect 10L) have significant activity at this pH and granular starch hydrolyzing enzymes (such as STARGEN) have significant activity at this pH. Similarly, all of these enzymes have significant activity in the temperature range of yeast (25° C. to 40° C.).

The harvest temperature of sugarcane, sorghum and maize can be below 20° C. However, the heat released by fermentation of sugars diffused out of parenchyma tissue will rapidly increase the temperature of this tissue to the temperature range where enzymes have significant activity.

The bulk density of whole-stalk sugarcane and sorghum is between 300 and 400 kg/m$^3$. The bulk density of billets (cut sections) of sugarcane, sorghum and maize (i.e. stalks) is between 180 and 240 kg/m$^3$. The bulk density of stalks chopped to between 10 mm and 25 mm in length is about 60 kg/m$^3$. In general, the bulk density is inversely related to the chopped length of the stalks.

If whole stalks, billets or chopped stalks are fermented in an aqueous solution, the juice in the stalks is diluted between 2.5× and 10×. Since the cost of separating ethanol from dilute solutions is prohibitive, this isn't practical. For instance, when the bulk density of stalks is 200 kg/m$^3$, 5 L of aqueous solution surrounds every 0.5 L of stalk juice. If 1 L of stalk juice has 10% sugar, it will have approximately 5% ethanol after fermentation. If stalks are fermented in an aqueous solution, the resulting solution will have 0.5% ethanol after fermentation, which isn't commercially viable to extract. This can be solved by fermenting whole stalks and billets in a 5% ethanol solution, but this has other problems of contaminant buildup over time.

Since transportation costs are primarily a function of volume (and not weight), and since crops are often harvested significant distances from where they're processed, it is quite expensive to transport sugars at such low bulk densities since only 2% to 5% of the volume of a truck is taken up by sugar. There is a need in the art to reduce the cost of making ethanol from sugar-rich crops by making ethanol at (or close to) the harvest site of these crops, reducing transportation costs.

Parenchyma cells in stalks are living tissue and therefore respire (breathe) after harvest. Respiration involves converting oxygen and sugar in the parenchyma cells to carbon dioxide and energy to maintain the cell. Sugarcane, sorghum and maize lose significant amounts of sugar to respiration when being stored. There is a need in the art to reduce the sugar lost to respiration by more rapidly converting sugars to ethanol than current methods. Once the sugars in crops are converted to ethanol, they can be stored for long periods, allowing continuous removal of the ethanol year round. It is desired to more efficiently use the capital invested in roller extraction, ethanol stripping and distillation by using this equipment year round, not just during the harvest season.

If sugarcane, sorghum and maize stalks are stored in anaerobic (without oxygen) conditions, microorganisms on the outside of the stalks will colonize the stalks and after 21 days will completely ferment all sugar in the stalks, mostly to lactic acid and acetic acid. Since the outer layer of the stalks are often abraded and damaged by harvesting, microorganisms can more easily penetrate the outer layers of the stalks, leading to sugar losses due to fermentation to lactic acid and acetic acid. Sprinkling stalks with yeast or lactic acid bacteria without chopping or shredding the stalks first is an ineffective ensiling technique.

Yeast produces large amounts of carbon dioxide while fermenting, and infusing yeast into cracked stalks forms a foam on the outside of the stalks during fermentation and expels liquid from the stalks by the action of bubble formation inside the tissue. Surprisingly, yeast do not get expelled by these bubbles, and the yeast can continue fermentation until all sugars are fermented.

Without wishing to be bound by any particular theory, it is believed that the adhesion of yeast cells to parenchyma cells in the presence of sugars is stronger than the forces of the carbon dioxide bubbles acting to expel the yeast from the parenchyma tissue.

This invention is also premised on the fact that the diffusion rate of sugars through the cell membrane in parenchyma cells of stalks of the Poaceae family is sufficient to enable fermentation organisms in the cracks to ferment the sugars within the parenchyma cells at a high rate. The ethanol then diffuses into the parenchyma cells. In some variations, pectin lyase macerates the parenchyma tissue, reducing the energy needed for crushing the stalks to recover the ethanol or unfermented sugars.

The invention provides a method for fermenting stalks of the Poaceae family, the method comprising the steps of:

(a) providing stalks of the Poaceae family, wherein the stalks have an average length greater than 100 mm, and wherein the stalks have an average initial moisture content between 25% and 80% (weight basis), such as 30%, 35%, 40%, 45%, 50%, 55%, 60%, 65%, 70%, or 75%;

(b) compressing the stalks between rollers while the stalks are submerged in an aqueous reagent solution, wherein the rollers compress the average diameter of the stalks by between 20% and 90%, and wherein the aqueous reagent solution contains one or more fermentation organisms selected from the group consisting of yeasts, lactic acid bacteria, acetic acid bacteria, and combinations thereof;

(c) removing the stalks from the aqueous reagent solution, wherein the stalks retain at least a portion of the one or more fermentation organisms; and (d) fermenting the stalks for a fermentation time to produce fermentation products within the stalks.

Stalks of the Poaceae family are brittle when they have a moisture content between 25% and 80%, so compressing them between rollers causes a fine network of cracks to form in the axial direction. The wild-type yeasts and lactic acid bacteria on the exterior of stalks aren't infused in significant numbers into the fine network of cracks in the stalks during step (b) because the concentration of fermentation organisms in the aqueous reagent solution is much higher than the concentration of those wild-type fermentation organisms from the exterior of the stalks. Neither yeasts nor lactic acid bacteria are motile, so the fermentation organisms from the exterior of the stalks don't colonize the interior of the stalks, and sugars diffusing from the interior of the stalks are consumed within the stalks by the fermentation organisms infused with the aqueous reagent solution. Therefore, very little sugar from the stalks is consumed by wild-type yeasts and lactic acid bacteria on the exterior of the stalks.

Stalks need to be long enough to be pulled in from a feed chute, propelled through rollers (either two rollers or three rollers in preferred embodiments) and ejected through an exit chute. The exit chute needs to have a constant (or increasing) diameter to prevent clogging on output. Tests have shown that 100 mm or longer stalks can work with rollers. Those skilled in the art will see that stalks can either be compressed one at a time between rollers or multiple stalks can be fed between rollers.

The key unit operation in this method is compressing the stalks while submerged in the aqueous reagent solution, just enough to form a network of microscopic cracks and not so much that a significant amount of juice is expressed. Surprisingly, stalks can be compressed while submerged at high velocity of the stalks, and the aqueous reagent solution is pulled into the network of microscopic cracks at this high velocity. Tests at 1 m/s cane velocity show that the submerged distance of about 200 mm has a submerged time of about 200 msec for the enzymes and fermentation organisms to penetrate the stalk. The Examples show that this time is sufficient to result in complete penetration of the stalk.

Different stalks of the Poaceae family (or different hybrids) require different amounts of pressure between rollers. Different roller diameters, different spring strengths, different paddle heights, different numbers of rollers and different tangential velocities will apply different crack propagation forces on different types of stalks. However, undue experimentation isn't required to determine the force required between rollers, since there are simple procedures for determining the optimal spring strength needed.

The simplest calibration test involves running stalks between rollers at the production velocity (between 0.1 and 10 m/s) with no liquid in the apparatus, changing springs with different spring constants until less than 1% juice loss is experienced. These juice loss tests can be done in a few hours. Tests have shown that only 0.5% juice loss occurs at sufficient pressure between rollers to effect complete infusion.

Those skilled in the art will realize that a subsequent validation test is measuring the brix of the juice in the stalk before infusion, infusing stalks with the aqueous reagent solution, and measuring the fermentation result after 3 days of fermentation. Measuring the ethanol content and softening of the parenchyma tissue will easily validate that the chosen pressure between rollers is effective.

The preferred embodiment of this invention is to compress whole stalks between rollers, since this can be done with inexpensive equipment and powered by manual labor, small internal compression motors or small electric motors. The energy required to compress is mostly used for crack propagation, which is especially energy-efficient. Those skilled in the art can see how to build other embodiments with rollers capable of industrial-scale infusion (more than 10 metric tons per hour).

When the stalks are compressed, the aqueous reagent solution flows into the network of microscopic cracks, distributing the fermentation organisms and the enzymes in the aqueous reagent solution throughout the parenchyma tissue of the stalks.

Stalks of the Poaceae family have a diameter about twice as large in the bottom ⅓ than the diameter in the top ⅓, and the compression pressure in the bottom ⅓ is about twice that in the top ⅓. This diameter profile (diameter as a function of distance from one end of the stalk) is reduced by rollers compressing the stalks to between 20% and 90% of the diameter at each point of the stalk, including 20%, 25%, 30%, 35%, 40%, 45%, 50%, 60%, 65%, 70%, 75%, 80%, 85% and 90%, with the most preferred range of between 40% and 60% of the diameter at each point of the stalk.

The rollers of the preferred embodiment of this invention need a force at the gap between the rollers proportional to the separation of the rollers. The preferred embodiment of this invention uses springs pushing or pulling the rollers together. Springs have the characteristic that the force supplied by the spring is linearly proportional to the displacement of the spring (Hooke's law).

The stalks don't bend easily before they pass through the rollers, and bend easily after they're compressed while passing through the rollers. In preferred embodiments of this invention, the rollers are oriented so the feed-in chute from above the aqueous reagent solution to below the aqueous reagent solution feeds straight into the rollers. In preferred embodiments of this invention, the chute leading out of the aqueous reagent solution causes the stalk to be bent in an upward direction after passing through the rollers. The preferred embodiment of this invention uses two rollers, but those skilled in the art will also realize that three rollers are a viable embodiment.

The rollers need to grab the stalks to feed them through the rollers. In preferred embodiments of this invention, the rollers have raised horizontal paddles to help pull the stalks through the rollers.

In preferred embodiments of this invention, a tank contains the aqueous reagent solution and has a feed valve that keeps the level of the aqueous reagent solution constant. Stalks passing through the aqueous reagent solution carry off some of the aqueous reagent solution, and tests have shown that water in the amount of about 15% of the mass of the stalk is carried off by absorption in the stalk, necessitating replenishment from the tank containing the aqueous reagent solution. This means that one ton of stalks will absorb about 150 liters of aqueous reagent solution. An embodiment of this invention has a pair of rollers to compress stalks in a perpendicular direction to rollers 107 and 108 in FIG. 1 before the stalks emerge into outlet tube 113, in order to squeeze out unneeded aqueous reagent solution absorbed by the stalks.

Yeast is the organism to produce ethanol from sugars in the parenchyma tissue and from the glucose liberated by enzymatic hydrolysis and dilute acid hydrolysis. This is used for sugar-rich stalks when the purpose of the fermentation is recovery of ethanol. Lactic acid bacteria is used to reduce the pH of the interior of the stalks to about 4.2, which prevents other organisms from colonizing the stalks. This is used when ensiling the stalks for subsequent consumption by ruminants. Co-cultures of yeast and acetic acid bacteria are used to convert sugars to acetic acid, in the case where the stalks are to be subsequently used for anaerobic digestion after ensiling. Co-cultures of mostly yeast with smaller amounts of lactic acid bacteria are used to both ferment sugars to ethanol and to preserve the stalks for subsequent consumption by ruminants.

In preferred embodiments, the stalks are selected from the group consisting of sugarcane stalks, sorghum stalks and maize stalks.

These are the most widely cultivated stalks of the Poaceae family.

In some embodiments, the stalks have leaves attached to the stalks.

When producing silage, the leaves are often more easily digested than the stalks and contain valuable nutrition for ruminants. The whole plant, with leaves attached, can be crushed between rollers to infuse the aqueous reagent solution into the stalks, while simultaneously treating the leaves with the same aqueous reagent solution. When compressing with leaves attached, it is preferred to feed the stalk into the rollers from the bottom of the stalk (the thick end) to the top of the stalk (the thin end), so that the leaves will fold against the stalk.

In some embodiments, the stalks are present as a whole plant.

When producing silage, it is sometimes useful to ensile the whole plant, including leaves and any grains attached to the whole plant. The compressing will also break open the sheath enclosing grains, making the grains more accessible to yeast and enzymes, and making the grains more digestible.

In preferred embodiments, the rollers have a tangential velocity between 0.1 m/s and 10 m/s.

Tests have shown that a tangential velocity of 1 m/s can infuse about 1 metric ton per hour of sweet sorghum stalks, resulting in more than 90% of the sugars in the stalks being fermented. Slower or faster tangential velocities can also provide complete infusion. Also, faster tangential velocities produce a finer network of cracks, as described in Skantz.

In preferred embodiments, the aqueous reagent solution contains enzymes selected from the group consisting of pectin lyase, amylase, cellulase, glucose oxidase, xylanase and combinations thereof.

Tests have shown that pectin lyase is useful for macerating parenchyma cell tissue in stalks of the Poaceae family, making it more efficient to extract juice by crushing.

Amylase is used in conjunction with pectin lyase to hydrolyze starch granules in parenchyma cells to glucose. Pectin lyase and/or xylanase macerate the parenchyma cells and cellulase bursts the parenchyma cells, allowing diffusion of the amylase to the starch granules.

Cellulase is used to hydrolyze cellulose in stalks to glucose, which is a way to slowly release glucose. Glucose in turn can be fermented to ethanol or lactic acid, and glucose oxidase can be used to convert glucose and $O_2$ to gluconic acid and hydrogen peroxide.

In some embodiments, the aqueous reagent solution contains acids selected from the group consisting of formic acid, acetic acid, lactic acid and combinations thereof.

Studies have shown that formic acid is effective in ensiling stalks of the Poaceae family. Acetic acid and lactic acid are useful as a pH buffer, and both prevent growth of unwanted microorganisms.

In some embodiments, the aqueous reagent solution contains ferrous ions, hydrogen peroxide or a combination thereof.

Ferrous ions are used with hydrogen peroxide in the Fenton reaction. Ferrous salts are soluble in water and can be safely fed to ruminants in the concentrations needed for the Fenton reaction. Some lactic acid bacteria produce hydrogen peroxide, hexose oxidases produce hydrogen peroxide from glucose, mannose and galactose and this hydrogen peroxide along with ferrous ions catalyze the breakdown of the lignocellulosic matrix, making it more digestible and accessible to enzymes. *Saccharomyces cerevisiae* can tolerate up to about 2 mM hydrogen peroxide, but lactic acid bacteria and acetic acid bacteria can't tolerate this concentration of hydrogen peroxide. This is described in Jamieson, DEREK J., "*Saccharomyces cerevisiae* has distinct adaptive responses to both hydrogen peroxide and menadione," Journal of bacteriology 174.20 (1992): 6678-6681, which is hereby incorporated by reference herein.

In preferred embodiments, the fermentation time is between 1 day and 7 days.

Tests have shown that complete fermentation takes between 1 day and 7 days, depending on the temperature and concentration of fermentation organisms.

Experiments have shown that the fermentation time with a concentration of yeast of about 2 cells per parenchyma cell results in a fermentation time of about 48 hours to 96 hours, but lower concentrations of yeast or lactic acid bacteria can take longer. Lower concentrations result in slower fermentation, which results in less increase in temperature, which reduces the need for expensive cooling mechanisms.

In preferred embodiments, the yeast is a strain of *Saccharomyces cerevisiae*.

*Saccharomyces cerevisiae* is the most widely used yeast for fermenting sugars to ethanol. This organism has the highest ethanol tolerance of any fermentation organism and many hybrids are available.

In some embodiments, the stalks are dehydrated during the fermentation lag time of step (d).

Dehydrating stalks during the fermentation lag time of step (d) evaporates water from the stalks, reducing the amount of water in the stalks at the end of fermentation in step (d). When the fermentation product is ethanol, this option results in a higher ethanol concentration in the juice of the stalks, which is more valuable than a lower ethanol concentration. When the fermentation product is lactic acid, this option results in a higher lactic acid concentration, which results in a lower pH and better ensiling. The increased exposed internal surface area of the stalks caused by the network of small cracks increases the rate of dehydration, since the rate of dehydration is proportional to the exposed surface area.

The fermentation lag time can be lengthened by decreasing the concentration of fermentation organisms in the aqueous reagent solution, thus increasing the total amount of water removed during the fermentation lag time. Heated air, radiative heating, conductive heating and combinations thereof add heat energy to the stalks during dehydration, with solar hot air being a preferred embodiment. Those skilled in the art will realize that there are numerous ways to maintain the temperature in the stalks below 38° C. during dehydration, especially by controlling the rate of circulation of hot air through the stalks. In some simple embodiments, stalks can be simply left to dry in the sun during the fermentation lag time, and later stored in an anaerobic environment for the majority of the fermentation time. The success of this simple embodiment depends on the temperature of the stalks not being raised above 38° C. during step (d) which would kill fermentation organisms infused into the fine network of cracks in the stalks.

During the fermentation lag time, little ethanol is produced, and mainly water from the stalks is removed by dehydration. The optimum amount of dehydration is such that the concentration of sugar in the stalks is the maximum that the fermentation organisms can ferment, such as about 32% sugar by weight with some strains of *Saccharomyces cerevisiae*. In some embodiments, the lactic acid bacteria are selected from the group consisting of *Lactobacillus plantarum, Lactobacillus buchneri, Pediococcus pentosaceus, Pediococcus acidilactici, Propionibacterium freudenreichii*, and combinations thereof.

These lactic acid bacteria are used in commercially available ensiling formulations.

In preferred embodiments, the method further comprises mixing the aqueous reagent solution using turbulent energy from 0.15 W/kg to 5 W/kg.

Sufficient turbulent energy is used so that the Kolmogorov length scale is on the order of less than the apoplast free length (e.g., about 20 microns). Using the Kolmogorov length scale, and knowing the kinematic viscosity of water at 20° C. is about $10^{-6}$ m$^2$/s, the energy required to mix the reagents and process water to a 20-micron scale requires about 5 W/kg, and mixing to a 50 micron scale requires about 0.15 W/kg. These scales are such that diffusion of sugars at this scale takes seconds and diffusion of enzymes at this scale takes minutes.

In some embodiments, the method further comprises maintaining the stalks in an anaerobic environment for an ensiling time subsequent to the completion of the fermentation time.

When the environment is anaerobic and there are either no sugars in the stalks and/or the pH is below 4.0, fungi and bacteria can't grow on the pectin or ethanol in the stalks.

In some embodiments, the ensiling time is between one day and one year.

During harvest time, there is little free time for processing of crops to remove sugars or ethanol, and ensiling is a method to spread the time-consuming processing of a crop over a whole year. In addition, if the crops are to be used as animal feed, they need to be ensiled for the whole period so they can be fed to ruminants until the next crop is harvested.

In preferred embodiments, the method further comprises recovering the fermentation products by crushing the stalks.

Pectin lyase macerates parenchyma tissue in stalks of the Poaceae family. This provides a retting action, where the liquid in the parenchyma cells can be more easily removed by crushing than by conventional crushing of untreated stalks.

In some embodiments, the method further comprises recovering the fermentation products by evaporation of the fermentation products from the stalks.

The rate of evaporation is proportional to the surface area of the exposed liquid, and the microscopic network of cracks in stalks in this invention expose a very large surface area per unit volume, making evaporation of ethanol efficient. In addition the concentration of ethanol in the evaporated vapor is higher than the concentration inside the stalks. This makes it practical to directly produce an alcoholic beverage from the evaporated vapor from the stalks.

An example of a solar still that will evaporate ethanol from the fermented stalks is described in U.S. Pat. No. 4,966,655, issued Oct. 30, 1990 to Wilkerson, which is hereby incorporated by reference herein. The sun heats the stalks by shining light through the plastic cover, and cool air at night causes condensation of the evaporated ethanol vapor. This solar still is sealed and will maintain an anaerobic environment because low levels of carbon dioxide will continue to be produced by fermentation, maintaining an internal positive pressure.

This type of solar still requires very little capital to build, and only the plastic cover sheet needs to be replaced every few years due to ultraviolet light degrading the plastic.

In some embodiments, the method further comprises feeding the stalks to ruminants subsequent to step (d).

Mechanically crushed and enzymatically degraded stalks are easier for ruminants to digest than uncrushed stalks. In addition, the yeast in the stalks increases the protein content. Further, the effect of dilute acid hydrolysis during ensiling causes the hemicellulose and cellulose to be more digestible.

In some embodiments, the method further comprises using the stalks with anaerobic digestion to produce methane subsequent to step (d).

Mechanically crushed and enzymatically degraded stalks are more efficiently used in anaerobic digestion than uncrushed stalks. In addition, the effect of dilute acid hydrolysis during ensiling causes the hemicellulose and cellulose to be more amenable to anaerobic digestion.

In some embodiments, the method further comprises using the stalks with enzymatic hydrolysis to produce ethanol from cellulose subsequent to step (d).

Mechanically crushed and enzymatically degraded stalks release more glucose during enzymatic hydrolysis than uncrushed stalks. In addition, the effect of dilute acid hydrolysis during ensiling causes the hemicellulose and cellulose to be more amenable to enzymatic hydrolysis.

A person of ordinary skill in the art will recognize that the temperature during fermentation can be limited to about 38° C. with a variety of low-cost techniques, especially if the fermentation takes place over 3 days, and that an initial temperature as low as 5° C. will suffice to start fermentation.

This low-temperature fermentation will quickly raise the temperature of the stalks to above 38° C.

A person of ordinary skill in the art will recognize that known apparatus may be employed for the processes, systems, and methods disclosed herein. The processes herein may be batch, continuous, semi-continuous, or pseudo-continuous. Any reference to "vessel" or "reactor" herein shall be construed to mean one or a plurality of such apparatus (such as in series or in parallel). Various flow patterns may be desired or observed. With chemical reactions and simultaneous mass-transfer processes involving multiple phases, the fluid dynamics can be quite complex. Depending on the specific design, flow patterns may approach plug flow or well-mixed flow.

The throughput, or process capacity, may vary widely from small laboratory-scale units to full commercial-scale biorefineries, including any pilot, demonstration, or semi-commercial scale. In various embodiments, the process capacity is at least about 1 kg/day, 10 kg/day, 100 kg/day, 1 ton/day (all tons are metric tons), 10 tons/day, 100 tons/day, 500 tons/day, 1000 tons/day, 2000 tons/day, or higher.

The overall system may be at a fixed location, or it may be made portable. The system may be constructed using modules which may be simply duplicated for practical scale-up.

Various probes may allow precise process monitoring and control across various stages of the process, up to and potentially including all stages of the process. Precise process monitoring would be expected to result in yield and efficiency improvements, both dynamically as well as over a period of time when operational history can be utilized to adjust process conditions (including pressure cycling programs). In some embodiments, a reaction probe is disposed in operable communication with a process zone. Such a reaction probe may be useful to extract liquid samples and analyze them, in order to determine extent of hydrolysis, or sugar profile, etc. Process adjustments may be based on measurements, if deemed necessary or desirable, using well-known principles of process control (feedback, feedforward, proportional-integral-derivative logic, etc.).

Solid, liquid, and gas streams produced or existing within the process can be independently recycled, passed to subsequent steps, or removed/purged from the process at any point.

EXAMPLES

The following examples demonstrate the principles of this invention. The infusion of yeast and enzymes by compressing while submerged, as described above, has been shown, by experimental evidence, to be useful for fermenting stalks in the Poaceae family.

The experimental apparatus of FIG. 1 is designed to reproduce industrial process functionality of the preferred embodiment of this invention as far as temperature, pressure, and flow control of an industrial unit. It was used at a sweet sorghum harvest at Delta BioRenewables sweet sorghum farm in Memphis, Tenn., USA in November, 2016 to test compressing freshly harvested stalks. Some stalks were then frozen and transported to Minneapolis, Minn., USA, and were thawed and subsequently compressed using this experimental apparatus, as described in Examples 2, 3 and 4 below. The mass loss caused by compression is described in Example 2 and the fermentation and enzymatic efficiency is described in Example 3 and 4.

FIG. 1 illustrates the device used. Cut stalks longer than 100 mm with no limit on maximum length are fed through the feeding tube 103. Vessel 101 contains the aqueous reagent solution. The stalk being fed into the device is first submerged into the solution and then comes into contact with rollers 108 and 107. Roller 108 is rotating free around shaft 109 which in turn is allowed to move vertically thanks to spring 111. The compression of the spring and the amount of movement of the roller can be adjusted using the tensioner 112, thereby allowing optimal treatment of stalks of various diameter and ensuring that the compression of the stalks is limited to between 20% and 90%. The shaft 114 of roller 107 cannot move vertically and it is driven by an external source of rotation. This external source of rotation is most typically an electric motor, but also can be a manual crank, bicycle crank or an internal combustion engine. Roller 107 provides increased friction and compression of the stalks. Metallic paddles 120 assist to propel the stalks through roller 107 and roller 108. Roller 107 drives the stalks between the two rollers and upon completing their passage through the system, the stalks are expelled through the outlet tube 113. As one stalk leaves the space between the rollers and therefore is not any longer driven by them, it is expelled by the system by being pushed by the next stalks being compressed between the rollers. The vessel 101 operates full of aqueous reagent solution, and provisions are made for the vessel to be kept full through the filler plug 122 and drained through the drain plug 121.

The experimental apparatus used a diameter of approximately 90 mm for roller 107, a diameter of approximately 100 mm for roller 108, a thickness and height of approximately 6 mm for metallic paddles 120, a minimum distance of 9.5 mm between roller 107 and roller 108, a tangential velocity of approximately 1 m/s for roller 107, a diameter of 100 mm for feeding tube 103 and outlet tube 113, and a length of 2 m for feeding tube 103 and outlet tube 113, The following examples use sweet sorghum from the Delta BioRenewables sweet sorghum farm in Memphis, Tenn., USA. Juice from sweet sorghum stalks was expressed by squeezing and sugar content in Brix was measured with a digital refractometer. The sweet sorghum stalks used had a moisture content of 70%.

Note that the Brix measurement of sweet sorghum juice was adjusted by multiplying Brix by about 0.8 to get the percentage by weight of total sugars. This is because sweet sorghum juice has more glucose and fructose than sugar beet or sugarcane juice, and the index of refraction of glucose and fructose differs from that of sucrose. This is described in Liu, Ronghou, Jinxia Li, and Fei Shen, "Refining bioethanol from stalk juice of sweet sorghum by immobilized yeast fermentation," *Renewable Energy* 33.5 (2008): 1130-1135, which is hereby incorporated by reference herein.

Four examples of this invention are shown below.

Example 1

Example 1 shows the difference between compressing one piece of sweet sorghum stalk between the jaws of a vice while submerged in an aqueous reagent solution and another piece while not submerged. Compressing while submerged results in 30% more fermentation than compressing while not submerged and then subsequently submerging.

Sweet sorghum was fermented, both with compressing 50% while submerged in an aqueous reagent solution and with compressing while in air and submerging in an aqueous reagent solution for 30 minutes.

A sweet sorghum stalk was used that was harvested at the Delta BioRenewables sweet sorghum farm in Memphis, Tenn., USA in October of 2015, transported in dry ice and stored in a freezer until tested in June of 2016. A sweet sorghum stalk was chosen from the freezer, 200 mm long and 10 mm in diameter. It was thawed in a refrigerator for two days. The stalk was cut into two 100 mm lengths, with the left sample weighing 7.1 g and the right sample weighing 9.4 g. A small amount of juice was expressed and the Brix was measured as 13%.

One liter of aqueous reagent solution was prepared by warming 1 liter of water to 38° C., then adding 1 g of Thermosacc yeast from Lallemand Biofuels & Distilled Spirits and 1 g of Fermax yeast nutrients from the BSG Corporation. This aqueous reagent solution was stirred with a magnetic stirrer for 30 minutes to rehydrate the freeze-dried yeast while the temperature of the aqueous reagent solution was maintained at 38° C.

The left sample was put into a plastic bag filled with the aqueous reagent solution, squeezed to a diameter of 5 mm and then immediately removed and allowed to drain. The mass of the left sample increased from 7.1 g to 7.5 g, an increase of about 5.6%.

The right sample was squeezed to a diameter of 5 mm when exposed to air, then weighed. The mass of the right sample reduced from 9.4 g to 8.7 g, a decrease of about 7.4%. The right sample was then submerged in the aqueous reagent solution for 30 minutes. Bubbles from the stalk were visible for 10 minutes. After 30 minutes, the mass of the right sample increased from 8.7 g to 9.3 g, an increase of about 6.9%.

The left and right samples were then put into two sealed PVC pipes, each about 100 mm long and with an inner diameter of 20.9 mm. These PVC pipes were then submerged in a water bath maintained at 38° C. and connected to a gas counter.

The progress of fermentation was measured by gas produced from each PVC pipe using two MilliGascounter, type MGC-1, from Dr.-Ing. Ritter Apparatebau GmbH & Co. KG in Bochum, Germany. The amount of gas produced is measured at the milliliter resolution over the period of the fermentation. The fermentation of 3.35 g of sugar (normally sucrose) generates 1 L of gas ($CO_2$), so the amount of sugar fermented, the rate of fermentation and the total amount of sugar fermented can be inferred by the graph of gas produced over time.

The left sample produced 0.0753 L of gas in 897 minutes (14.95 hours). The right sample produced 0.0767 L of gas in 942 minutes (15.7 hours).

After completion of fermentation, juice was squeezed from each sample, and the Brix of the left sample was 2.6 and the Brix of the right sample was 4.2. The pH of the left sample was 3.98 and the pH of the right sample was 3.61.

To compute the sugar content of sweet sorghum juice from the Brix measurement, we multiplied the Brix of 13% by 0.8, resulting in a sugar content of the juice of about 10.4%. This is because sweet sorghum juice has more glucose and fructose than sugarcane juice, and the index of refraction of glucose and fructose differs from that of sucrose. This is described in Liu et al., "Refining bioethanol from stalk juice of sweet sorghum by immobilized yeast fermentation," *Renewable Energy* 33.5 (2008): 1130-1135, which is hereby incorporated by reference herein.

To compute the sugar content of each stalk, we assume a moisture content of about 70%, resulting in an estimate of 8.3% of the stalk mass of sugar. Given that the left sample had a mass of 7.1 g before compressing, and assuming a loss of 7% of sugars due to compressing, results in an estimate of 0.55 g of sugar in the left sample. Similarly, the right sample had a mass of 9.4 g before compressing, resulting in an estimate of 0.73 g of sugar in the right sample.

The left sample produced 0.55 g/0.0753 L=7.3 g/L (49% efficiency) while the right sample produced 0.73 g/0.0767 L=9.5 g/L (35% efficiency). This shows that the efficiency of this invention is significantly higher than the alternative approach of fracturing the sweet sorghum and subsequently submerging it. In addition, this shows that this invention infuses the aqueous reagent solution into the stalk at least 100 times faster than the alternative approach (a few seconds instead of 10 minutes), which is critical because of the need for rapid infusion of crops as they are harvested.

Example 2

Example 2 shows the mass loss when compressing sweet sorghum stalks using the apparatus described in FIG. 1 at 1 m/s between rollers while not submerged. This compression used a high spring load (tensioner 112 turned to compress spring 111 5 mm past zero resting spring pressure) and a low spring load (tensioner 112 turned to compress spring 111 to zero resting spring pressure). This low spring load was used in Example 3 and this high spring load was used in Example 4.

The experimental procedure was:
(1) cut eight 600 mm sections of sweet sorgum
(2) record mass and average diameter
(3) set tensioner 112 to 5 mm past zero resting spring pressure
(4) feed 4 sections of sorghum and record mass
(5) set tensioner 112 to zero resting spring pressure
(6) feed 4 sections of sorghum and record mass The springs used in these experiments had a Hooke's law spring constant of 17.4 kN/m, measured by adding weights in 2 kg increments to the springs and measuring the displacement of the spring. The curve was quite linear, with 24 kg of weight (235.36 N) compressing the spring from 52.2 mm to 38.7 mm (13.5 mm compression).

The measured diameter reduction and calculated crush force on a 20 mm stalk are shown in Table 1. This shows that under high spring load (5 mm spring compression), a 20 mm stalk was compressed 75% between paddles 120 and roller 108 and was compressed 45% between roller 107 and roller 108.

TABLE 1

Diameter reduction and crush force

| Spring Load | Diameter under paddles (mm) | Diameter between rollers (mm) | Diameter reduction under paddles (%) | Diameter reduction between rollers (%) | Crush force under paddles (MPa) | Crush force between rollers (MPa) |
| --- | --- | --- | --- | --- | --- | --- |
| High | 4.9 | 10.89 | 75.50% | 45.55% | 5.84 | 0.79 |
| Low | 7.1 | 12.74 | 64.50% | 36.30% | 5.20 | 0.63 |

Table 2 shows that for a high spring load (5 mm spring compression), there was a mass loss of an average of 0.35% and for a low spring load (0 mm spring compression), there was a mass loss of an average of 0.24%. This low spring load is used in Example 3 and this high spring load is used in Example 4. Note that in Example 2, there was 7% juice loss with 50% compression of the stalk. This example demonstrates that compressing between rollers at 1 m/s results in significantly less loss of juice than simply static compression of the stalk.

TABLE 2

Mass loss with compression

| Sample | Spring load | Initial mass (g) | Mass Crushing (g) | After Diameter (mm) | Average Mass loss (%) |
|---|---|---|---|---|---|
| 1 | High | 127.4 | 127.0 | 16 | 0.31% |
| 2 | High | 127.3 | 126.9 | 18 | 0.31% |
| 3 | High | 174.5 | 174.0 | 19 | 0.29% |
| 4 | High | 193.1 | 192.2 | 21 | 0.47% |
| 5 | Low | 137.0 | 136.8 | 17 | 0.15% |
| 6 | Low | 183.2 | 182.7 | 24 | 0.27% |
| 7 | Low | 150.3 | 150.2 | 20 | 0.07% |
| 8 | Low | 105.1 | 104.6 | 15 | 0.48% |

Example 3

Example 3 shows the result of fermentation after compressing between rollers with low spring load with four different enzyme combinations (none, HTec3, Pectinex XXL and HTec3 and Pectinex XXL). This demonstrates that fermentation is successful with a low spring load, but that enzymatic action is ineffective. Without wishing to be bound by any particular theory, it is believed that the low spring load produced a less extensive network of cracks in the stalks than the high spring load, and the average diffusion distance for the enzymes was longer than the fermentation time, while the significantly faster diffusion speed of sugars led to complete diffusion of sugars to the yeast cells, albeit at longer distances.

Table 3 shows the yeast and enzyme composition of samples 1-4 in Example 3 and Example 4.

TABLE 3

Yeast and enzymes used in Examples 3 and 4

| Sample | Yeast 5 g/L | Htec3 5 g/L | Pectinex 5 g/L | pH |
|---|---|---|---|---|
| 1 | X |   |   | 5.15 |
| 2 | X | x |   | 5.07 |
| 3 | X |   | x | 5.16 |
| 4 | X | x | x | 5.12 |

Table 4 shows the results of fermenting stalks with low spring load. There was no visible softening of parenchyma tissue in any of these samples after fermentation completed.

TABLE 4

Fermentation results of Example 3

| Sample | Initial mass (g) | Mass After Infusion (g) | Mass After Fermenting (g) | Brix (%) | Gas (L) | Efficiency (%) |
|---|---|---|---|---|---|---|
| 1 | 122.0 | 137.3 | 126.7 | 20.0 | 3.839 | 94.11% |
| 2 | 100.3 | 122.7 | 102.5 | 20.8 | 3.115 | 89.32% |
| 3 | 117.1 | 136.7 | 126.3 | 19.8 | 3.843 | 99.15% |
| 4 | 92.4 | 106.6 | 97.3 | 20.4 | 2.944 | 93.44% |

Example 4

Table 5 shows the results of fermenting stalks with high spring load. After fermentation, the parenchyma tissue of sample 1 was not softened, sample 2 was moderately softened, and the parenchyma tissue of samples 3 and 4 were completely dissolved. This demonstrates that both fermentation and enzymatic action are effective with a high spring load. Without wishing to be bound by any particular theory, it is believed that the efficiencies above 100% were caused by enzymatic hydrolysis of cellulose in the stalks by the cellulase in HTec3.

Juice from these four samples was expressed with a commercial sugarcane press juicer and sent for analysis of methanol content to Galbraith Laboratories, Inc. in Knoxville, Tenn., USA using procedure GC-100H. Sample 1 had 42 ppm, sample 2 had 35 ppm, sample 3 had 64 ppm and sample 4 had 70 ppm of methanol in the expressed juice. This shows that methanol production during in-stalk fermentation is very limited, and that Pectinex XXL produces very modest amounts of methanol.

TABLE 5

Fermentation results of Example 4

| Sample | Initial mass (g) | Mass After Infusion (g) | Mass After Fermenting (g) | Brix (%) | Gas (L) | Efficiency (%) |
|---|---|---|---|---|---|---|
| 1 | 135.5 | 162.4 | 148.7 | 21.5 | 4.3114 | 88.53% |
| 2 | 125.5 | 147.9 | 133.9 | 16.8 | 3.9086 | 110.90% |
| 3 | 209.6 | 229.9 | 217.0 | 17.9 | 6.4593 | 102.99% |
| 4 | 157.5 | 183.5 | 169.7 | 15.6 | 4.2665 | 103.88% |

In this detailed description, reference has been made to multiple embodiments and to the accompanying drawings in which are shown by way of illustration specific exemplary embodiments of the invention. These embodiments are described to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and FIGUREs described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims. In the case of conflict in definitions between the present disclosure and a dictionary or other reference, the present disclosure will be controlling.

What is claimed is:

1. A method for fermenting stalks of the Poaceae family, said method comprising the steps of:
   (a) providing stalks of the Poaceae family, wherein said stalks have an average length greater than 100 mm, and wherein said stalks have an average initial moisture content between 25% and 80%;
   (b) compressing said stalks between rollers while said stalks are submerged in an aqueous reagent solution, wherein said rollers compress the average diameter of said stalks by between 20% and 90%, and wherein said aqueous reagent solution contains one or more fermentation organisms selected from the group consisting of yeasts, lactic acid bacteria, acetic acid bacteria, and combinations thereof;

(c) removing said stalks from said aqueous reagent solution, wherein said stalks retain at least a portion of said one or more fermentation organisms; and (d) fermenting said stalks for a fermentation time to produce fermentation products within said stalks.

2. The method of claim 1, wherein said stalks are selected from the group consisting of sugarcane stalks, sorghum stalks and maize stalks.

3. The method of claim 1, wherein said stalks have leaves attached to said stalks.

4. The method of claim 1, wherein said stalks are present as a whole plant.

5. The method of claim 1, wherein said rollers have a tangential velocity between 0.1 m/s and 10 m/s.

6. The method of claim 1, wherein said aqueous reagent solution contains enzymes selected from the group consisting of pectin lyase, amylase, cellulase, glucose oxidase, hexose oxidase, xylanase, and combinations thereof.

7. The method of claim 1, wherein said aqueous reagent solution contains acids selected from the group consisting of formic acid, acetic acid, lactic acid, and combinations thereof.

8. The method of claim 1, wherein said aqueous reagent solution contains ferrous ions, hydrogen peroxide, or a combination thereof.

9. The method of claim 1, wherein said fermentation time is between 1 day and 7 days.

10. The method of claim 1, wherein said yeast is a strain of *Saccharomyces cerevisiae*.

11. The method of claim 1, wherein said stalks are dehydrated during a fermentation lag time of step (d).

12. The method of claim 1, wherein said lactic acid bacteria are selected from the group consisting of *Lactobacillus plantarum, Lactobacillus buchneri, Pediococcus pentosaceus, Pediococcus acidilactici, Propionibacterium freudenreichii*, and combinations thereof.

13. The method of claim 1, said method further comprising mixing said aqueous reagent solution using turbulent energy from 0.15 W/kg to 5 W/kg.

14. The method of claim 1, said method further comprising maintaining said stalks in an anaerobic environment for an ensiling time subsequent to the completion of said fermentation time.

15. The method of claim 14, wherein said ensiling time is between one day and one year.

16. The method of claim 1, wherein said method further comprises recovering said fermentation products by crushing said stalks.

17. The method of claim 1, wherein said method further comprises recovering said fermentation products by evaporation of said fermentation products from said stalks.

18. The method of claim 1, wherein said method further comprises feeding said stalks to ruminants subsequent to step (d).

19. The method of claim 1, wherein said method further comprises using said stalks with anaerobic digestion to produce methane subsequent to step (d).

20. The method of claim 1, wherein said method further comprises using said stalks with enzymatic hydrolysis and fermentation to produce ethanol from cellulose subsequent to step (d).

* * * * *